(12) United States Patent
Ueki et al.

(10) Patent No.: US 7,580,133 B2
(45) Date of Patent: Aug. 25, 2009

(54) INTERFEROMETRIC APPARATUS FOR MEASURING MOVING OBJECT AND OPTICAL INTERFEROMETRY METHOD FOR MEASURING MOVING OBJECT

(75) Inventors: Nobuaki Ueki, Saitama (JP); Hidenori Takahashi, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 175 days.

(21) Appl. No.: 11/447,164

(22) Filed: Jun. 6, 2006

(65) Prior Publication Data

US 2007/0002333 A1    Jan. 4, 2007

(30) Foreign Application Priority Data

Jun. 16, 2005    (JP) .......................... P.2005-177051

(51) Int. Cl.
  *G01N 21/84* (2006.01)
  *G01B 11/02* (2006.01)
(52) U.S. Cl. ........................ 356/511; 356/429
(58) Field of Classification Search ......... 356/429–431, 356/479, 511–516; 250/214 RC, 214 SW, 250/227.19, 227.27, 559.01, 559.03, 227.21
See application file for complete search history.

(56) References Cited

U.S. PATENT DOCUMENTS

| | | | | |
|---|---|---|---|---|
| 3,871,773 A * | 3/1975 | Shaw, Jr. | ..................... | 356/431 |
| 4,334,779 A * | 6/1982 | Domey et al. | ................ | 356/496 |
| 5,361,131 A * | 11/1994 | Tekemori et al. | ............ | 356/499 |
| 6,769,792 B1 * | 8/2004 | Bornhorst | ................... | 362/293 |
| 7,054,013 B2 * | 5/2006 | Schyns et al. | ............... | 356/429 |
| 7,173,703 B2 * | 2/2007 | Hosel et al. | .................. | 356/429 |
| 7,177,029 B2 * | 2/2007 | deGroot | ....................... | 356/497 |
| 7,317,542 B2 * | 1/2008 | Krambeer et al. | ........... | 356/603 |
| 7,382,457 B2 * | 6/2008 | Kiraly | ......................... | 356/430 |
| 2005/0007599 A1 * | 1/2005 | deGroot | ....................... | 356/511 |

OTHER PUBLICATIONS

Harris et al., "Stroboscopic interferometer," Jul. 15, 1979, Applied Optics, vol. 18, No. 14, pp. 2368-2371.*
De Groot, "Stroboscopic white-light interference microscopy," Applied Optics, Aug. 10, 2006, vol. 45, No. 23, pp. 5840-5844.*
Piyaket et al., "Programmable ultrashort optical pulse delay using an acousto-optic deflector," Applied Optics, Mar. 10, 1995, vol. 34, No. 8, pp. 1445-1453.*
Steinmeyer, "A review of ultrafast optics and optoelectronics," Journal of Optics: Pure and Applied Optics, 2003, vol. 5, pp. R1-R15.*

* cited by examiner

*Primary Examiner*—Gregory J Toatley, Jr.
*Assistant Examiner*—Scott M Richey
(74) *Attorney, Agent, or Firm*—Birch, Stewart, Kolasch & Birch, LLP (57) ABSTRACT

A moving-object measuring interferometric apparatus comprises: a light beam output section outputting a measuring beam; an interference optical system obtaining interference light by projecting the measuring beam onto an object and by allowing light reflected from the object or transmitted light having passed through the object to interfere with reference light; an image pickup section obtaining image information by receiving the interference light on an image pickup surface; and an image pickup timing control section setting a momentary image pickup period during which the object is regarded as being stationary to be contained in a light reception acceptable period of the image pickup surface and controlling the interference light to enter the image pickup surface only during the momentary image pickup period.

14 Claims, 2 Drawing Sheets

INTERFEROMETRIC APPARATUS FOR MEASURING MOVING OBJECT AND OPTICAL INTERFEROMETRY METHOD FOR MEASURING MOVING OBJECT

BACKGROUND OF THE INVENTION

1. Field of the Invention

The present invention relates to an interferometric apparatus and an optical interferometry method for obtaining surface-shape information about an object to be inspected or phase information, such as refractive-index distribution, about a transparent object to be inspected. More specifically, the present invention relates to a moving-object measuring interferometric apparatus and an optical interferometry method for measuring a moving object that are suitable for the optical interferometric measurement of a to-be-inspected object moving with respect to the interferometric apparatus (note that the term "moving" includes the deformation of the surface of a to-be-inspected object and a change in the refractive-index distribution of the object, as well as a spatial position change and a rotational movement).

2. Description of the Related Art

A speckle interferometric apparatus for measuring the time-dependent deformation (i.e., deformation caused with the lapse of time) of an object to be inspected is generally used as the related-art apparatus for optically measuring a to-be-inspected object involving a movement. In an apparatus for measuring moire fringes, a case is also known in which a moving object to be inspected is intermittently subjected to strobe irradiation so as to obtain a moire-fringe image taken at each irradiation time.

Additionally, a proposal has been made for providing an interferometric apparatus in which a cyclically moving object to be inspected is intermittently irradiated with short pulse light synchronously with the movement cycle of the object, and reflected light obtained by each irradiation is subjected to multiple exposure, thus obtaining interference-fringe images taken at the same position of the object (see JP-A-2003-222508).

In recent years, a desire has increased to measure a to-be-inspected object moving along a production line according to the optical interferometry in an in-line (on-process) state. For example, in an industry to produce film materials (made of polyester resin, such as PET or PEN, polycarbonate resin, amorphous polyolefin resin, or acrylic resin) that are used for a liquid crystal display or a plasma display, there is a desire to measure the thickness non-uniformity of a film material, which depends on a manufacturing environment or a manufacturing condition, in an in-line manner at intervals of a predetermined time at a predetermined position of a production line along which the film material flows and to feed back the measurement results for controlling the manufacturing condition or the like.

For example, a method disclosed by JP-A-59-105508 is known as the related-art method for measuring the thickness non-uniformity or the like of a to-be-inspected object shaped like a highly transparent film according to the optical interferometry. However, the related-art method is based on the measurement in an off-line state, and is not based on the measurement of a to-be-inspected object moving along a production line according to the optical interferometry.

Additionally, a method disclosed by JP-A-2003-222508 mentioned above is invented for a to-be-inspected object that reciprocates cyclically, and has a problem in the fact that parts to be measured, such as those of the film material mentioned above, are moved in sequence, and hence that of JP-A-2003-222508 cannot be applied to a to-be-inspected object the same part of which has difficulty in being photographed many times.

SUMMARY OF THE INVENTION

The present invention has been made in consideration of these circumstances, and, therefore, it is an object of the present invention to provide an interferometric apparatus for measuring a moving object and an optical interferometry method for measuring a moving object that are capable of performing the optical interferometric measurement of a to-be-inspected object whose part to be measured is moved in sequence.

To solve the problems, in the present invention, interference light is allowed to enter an image pickup surface only during a momentary image pickup period that is set in a light reception acceptable period of the image pickup surface, so that interference-fringe image information that has phase information about a to-be-inspected object during the momentary image pickup period can be obtained.

In more detail, the interferometric apparatus of the present invention is a moving-object measuring interferometric apparatus for measuring a moving to-be-inspected object by optical interferometry, the apparatus comprising: a light beam output section that outputs a measuring beam; an interference optical system that obtains interference light by projecting the measuring beam onto the to-be-inspected object moving with respect to the interferometric apparatus and by allowing to-be-inspected reflected light reflected from the to-be-inspected object or to-be-inspected transmitted light having passed through the to-be-inspected object to interfere with reference light; an image pickup section that obtains image information by receiving the interference light on an image pickup surface; and an image pickup timing control section that sets a momentary image pickup period during which the to-be-inspected object can be regarded as being substantially stationary with respect to the interferometric apparatus so as to be contained in a light reception acceptable period of the image pickup surface and controls the interference light so that the interference light enters the image pickup surface only during the momentary image pickup period; wherein the interference light received on the image pickup surface during the momentary image pickup period enables the image pickup section to obtain interference-fringe image information that has phase information about the to-be-inspected object during the momentary image pickup period.

Preferably, in the moving-object measuring interferometric apparatus of the present invention, the image pickup timing control section changes an emitted direction of the measuring beam so that the measuring beam is projected onto the to-be-inspected object only during the momentary image pickup period, and the image pickup timing control section comprises a light deflecting section that changes the emitted direction of the measuring beam by an acoustooptic effect.

Preferably, in terms of the movement amount of the to-be-inspected object during the momentary image pickup period, the momentary image pickup period corresponds to less than half the pixel size of the image pickup surface on the image pickup surface.

The moving-object measuring interferometric apparatus of the present invention can further comprise a transmission type reference plate disposed on an optical path of the measuring beam. The measuring beam admitted to a reference surface of the transmission type reference plate is divided into a light beam that is reflected in an opposite direction by the reference surface so as to serve as the reference light and a light beam that passes through the reference surface so as to irradiate the to-be-inspected object. Preferably, in a case where the to-be-inspected object is transparent with respect to the measuring beam, the moving-object measuring interferometric apparatus further comprises a reflecting plate disposed to substantially face the transmission type reference plate in a state of situating the to-be-inspected object between the reflecting plate and the transmission type reference plate. The measuring beam that has passed through the to-be-inspected object and that has entered a reflecting surface of the reflecting plate is reflected toward the transmission type reference plate.

Preferably, in the interferometric apparatus, a light-quantity ratio adjusting film is attached to the reference surface of the transmission type reference plate. The light-quantity ratio adjusting film includes at least one light reflection absorbing layer and at least one dielectric reflection preventing layer stacked on the reference surface of the transmission type reference plate in this order when viewed from the reference plate. The light-quantity ratio adjusting film has a function to reflect a part of the measuring beam that enters from a side of the reference surface and to absorb a remaining part thereof and emit a still remaining part thereof toward the to-be-inspected object. The light-quantity ratio adjusting film further has a function to absorb a part of return light from the reflecting plate that enters from a side of the to-be-inspected object and to emit a remaining part thereof toward the reference surface so as to serve as the to-be-inspected transmitted light while being controlled not to be reflected. Preferably, a highly reflective film that reflects the measuring beam with high reflectance is attached to the reflecting surface of the reflecting plate.

Instead of this form, a light-quantity ratio adjusting filter can be removably disposed between the reference surface of the transmission type reference plate and the to-be-inspected object, and a highly reflective film that reflects the measuring beam with high reflectance can be attached to the reflecting surface of the reflecting plate. The light-quantity ratio adjusting filter is provided with a light-quantity ratio adjusting film having a multi-layer film structure. The light-quantity ratio adjusting film includes at least one light reflection absorbing layer and at least one dielectric reflection preventing layer stacked either on a surface of a transparent substrate facing the to-be-inspected object or on a surface of the transparent substrate facing the reference surface in this order when viewed from the reference surface The light-quantity ratio adjusting film has a function to reflect a part of incident light coming from a side of the surface of the transparent substrate facing the reference surface and to absorb a remaining part thereof and emit a still remaining part thereof toward the to-be-inspected object. The light-quantity ratio adjusting film further has a function to absorb a part of return light from the to-be-inspected object coming from a side of the surface of the transparent substrate facing the to-be-inspected object and to emit a remaining part thereof toward the reference surface so as to serve as the to-be-inspected light while being controlled not to be reflected.

The moving-object measuring interferometric apparatus of the present invention can further comprise an analysis section that makes a fringe analysis based on the interference-fringe image information so as to obtain the phase information. Preferably, if the momentary image pickup periods are set during a predetermined time, the analysis section is structured so that each fringe analysis based on the interference-fringe image information obtained during each momentary image pickup period can be performed in a parallel manner.

The analysis section can make the fringe analysis according to a Fourier transform analysis method. Preferably, in this case, the interference optical system is disposed so that spatial carrier fringes required for the Fourier transform analysis method are superimposed on the interference light.

Preferably, in a case where the to-be-inspected object has fringe-like patterns that extend in substantially parallel with each other, the interference optical system is disposed so that the spatial carrier fringe becomes substantially perpendicular to the fringe-like pattern. Preferably, in a case where the to-be-inspected object has optical anisotropy, the measuring beam is formed to be linearly-polarized light, and the oscillation direction in an electric field of the linearly polarized light is adjusted in accordance with a direction of an optical axis of the to-be-inspected object so as to restrain birefringence.

The optical interferometry method of the present invention is an optical interferometry method for measuring a moving to-be-inspected object while using an interferometric apparatus, and is characterized by comprising a light beam output step of outputting a measuring beam; an interference light generation step of obtaining interference light by projecting the measuring beam onto the to-be-inspected object moving with respect to the interferometric apparatus and by allowing to-be-inspected reflected light reflected from the to-be-inspected object or to-be-inspected transmitted light that has passed through the to-be-inspected object to interfere with reference light; an image pickup step of receiving the interference light by an image pickup surface so as to obtain image information; and an image pickup timing control step of setting a momentary image pickup period during which the to-be-inspected object can be regarded as being substantially stationary with respect to the interferometric apparatus to be contained in a light reception acceptable period of the image pickup surface and controlling the interference light so that the interference light enters the image pickup surface only during the momentary image pickup period. In the optical interferometry method, interference-fringe image information that has phase information about the to-be-inspected object during the momentary image pickup period is obtained by the interference light received at the image pickup surface during the momentary image pickup period. The phase information is obtained by making a fringe analysis based on the interference-fringe image information obtained thereby.

In the present invention, the "light reception acceptable period of the image pickup surface" corresponds to a single charge-storage period determined by shutter speed or by an electric-charge readout method, for example, in a case where a principal element of the image pickup surface is a CCD image sensor or a CMOS image sensor (for example, in a solid-state image sensor according to the field readout method of the NTSC standard, single charge-storage period is a period of 1/60 second or, if the shutter speed for a still image is set in a predetermined period (e.g., 1/120 second), the single charge-storage period corresponds to this).

The term "move" used in this description denotes a situation in which a to-be-inspected object is rotated or deformed, a situation in which a to-be-inspected object makes complex movements that include a rotational movement or a deformed movement, or a situation in which the characteristics (e.g., refractive-index distribution) of the inside of a transparent to-be-inspected object are changed, as well as a situation in which the whole of a to-be-inspected object spatially shifts its position and a situation in which a long to-be-inspected object flows in one direction.

In the present invention, various objects that move in a variety of manners can be employed as objects to be measured. The present invention can be suitably applied especially when a long object (for example, a transparent film material) that extends in one direction and that moves in its extension direction is measured at a fixed point at intervals of a predetermined time.

DETAILED DESCRIPTION OF THE INVENTION

Figure 1:
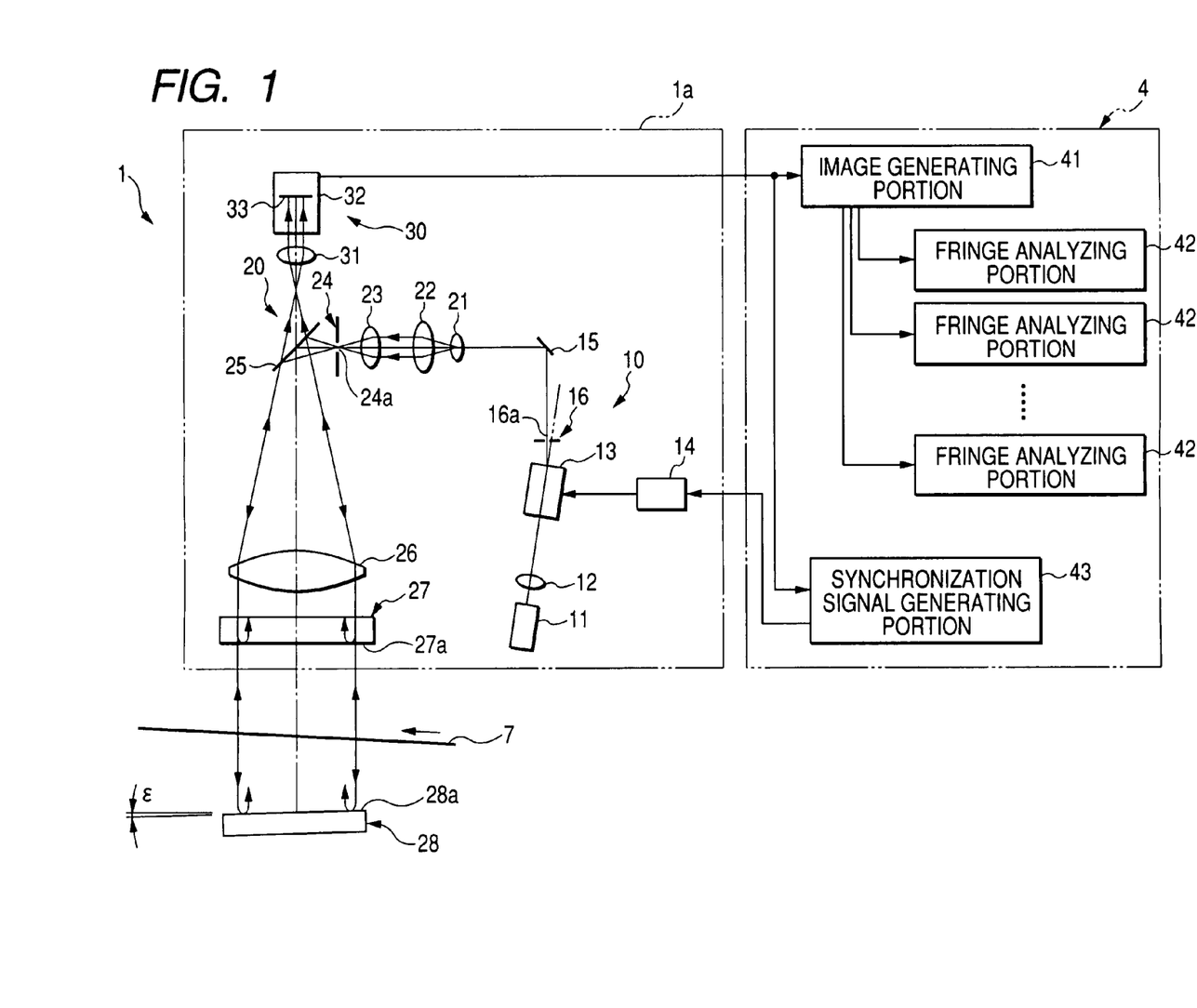
FIG. 1 is a schematic view of a main part of a moving-object measuring interferometric apparatus according to an embodiment of the present invention.

An embodiment of the present invention will be hereinafter described with reference to the accompanying drawings. FIG. 1 is a schematic view showing a structure of a principal part of a moving-object measuring interferometric apparatus according to an embodiment of the present invention, and FIG. 2 shows an arrangement of elements formed when the in-line measurement is performed.

Figure 2:
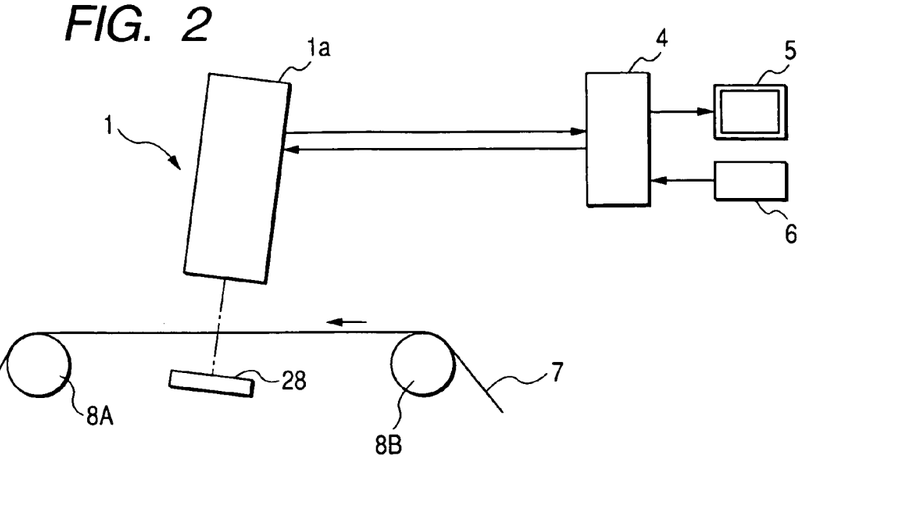
FIG. 2 shows the interferometric apparatus of FIG. 1 arranged during in-line measurement.

As shown in FIG. 2, the moving-object measuring interferometric apparatus according to this embodiment (hereinafter, also referred to as the "apparatus of the present embodiment") is used to perform the in-line measurement of a to-be-inspected object 7 that is a long film material (made of, for example, polyester resin, such as PET or PEN, polycarbonate resin, amorphous polyolefin resin, or acrylic resin) that is transparent with respect to a measuring beam during the manufacturing process thereof. The interferometric apparatus is made up of an interferometer 1, an analyzer 4, which is, for example, a computer device, an image display device 5, and an input device 6, which is, for example, a mouse or a keyboard.

The interferometer 1 allows the to-be-inspected object 7 conveyed at a speed of, for example, approximately 1 m/s along the production line to undergo stationary measurement at intervals of a predetermined time between two carrier rollers 8A and 8B so as to intermittently obtain interference-fringe image information that includes phase information, such as thickness non-uniformity information, about the object 7. As shown in FIG. 2, the interferometer 1 is disposed so that the to-be-inspected object 7 conveyed substantially horizontally from the right to the left is interposed between an interferometer housing 1a and a flat reflecting plate 28 and so that the axis line (shown by the alternate long and short dash line) of a measuring beam emitted from the housing 1a becomes oblique with respect to the object 7 (in order to prevent light reflected from the object 7 from acting as noise light).

As shown in FIG. 1, the interferometer 1 includes, inside the housing 1a, a light beam output section 10 that outputs a measuring beam, a Fizeau interference optical system 20 that obtains interference light by projecting a measuring beam onto the object 7 moving with respect the interferometer 1 and by producing interference between to-be-inspected transmitted light that has passed through the object 7 and has been reflected from the flat reflecting plate 28 and reference light, and an image pickup section 30 that receives the interference light on an image-pickup surface so as to obtain image information.

Among these elements, the light beam output section 10 is made up of a semiconductor laser light source 11 that emits a highly coherent light beam, a collimator lens 12 that collimates the light beam emitted from the semiconductor laser light source 11 so as to produce a measuring beam, an AOM (acoustooptic modulator) 13 serving as a light deflecting section that switches the emitted direction of the measuring beam emitted from the collimator lens 12 by an acoustooptic effect, an AOM driver 14 that drives the AOM 13, a reflecting mirror 15 that reflects a measuring beam (more specifically, its first-order diffracted light) emitted from the AOM 13 toward the interference optical system 20, and a slit plate 16 disposed on an optical path between the reflecting mirror 15 and the AOM 13 (note that the slit plate 16 has a slit 16a through which only the first-order diffracted light of the measuring beam emitted from the AOM 13 toward the reflecting mirror 15 passes). The AOM 13, the AOM driver 14, and a synchronization signal generating portion 43 described later constitute an image pickup timing control section that switches the emitted direction of the measuring beam so that the measuring beam is projected onto the to-be-inspected object 7 only during a momentary image pickup period (for example, 10 μs) during which the object 7 can be regarded as being substantially stationary with respect to the interferometer 1. Only during the momentary image pickup period, the measuring beam can enter the reflecting mirror 15.

On the other hand, the interference optical system 20 includes a beam expander including a divergent lens 21 and a collimator lens 22, a convergent lens 23 that converges a measuring beam emitted from the collimator lens 22, and a pinhole plate 24 having a pinhole 24a disposed at a convergent point of the measuring beam converged by the convergent lens 23. The interference optical system 20 further includes a beam splitter 25 that splits the measuring beam passing through the pinhole 24a into two beam parts and that reflects one of the beam parts downwardly in FIG. 1, a collimator lens 26 that collimates the measuring beam reflected from the beam splitter 25, a transmission type reference plate 27 that is disposed on the optical path of the measuring beam emitted from the collimator lens 26 and that divides the measuring beam emitted from the collimator lens 26 into a light beam that is reflected in an opposite direction at its reference surface 27a so as to serve as a reference light beam and a light beam that passes through the reference surface 27a so as to irradiate the object 7 therewith, and the flat reflecting plate 28 mentioned above that is disposed to almost exactly face the reference plate 27 with the object 7 between the reference plate 27 and the reflecting plate 28 and that reflects the measuring beam that has passed through the object 27 at its reflecting surface 28a (which has been smoothed with high accuracy so that the wave front of incident light can be maintained) toward the reference plate 27.

A light-quantity ratio adjusting film including at least one light reflection absorbing layer and at least one dielectric reflection preventing layer is attached to the reference surface 27a of the transmission type reference plate 27. A highly reflective film (which is made of a metal film, such as an aluminum film, or a dichroic film) having high reflectance with respect to a measuring beam is attached to the reflecting surface 28a of the flat reflecting plate 28. Herein, the light-quantity ratio adjusting film has a function to reflect a part of a measuring beam coming from the back surface of the reference plate 27 (i.e., from the surface facing the reference surface 27a) and to absorb a part of the remaining part and then emit a still remaining part of the measuring beam toward the to-be-inspected object 7. The light-quantity ratio adjusting film further has a function to absorb a part of return light returned from the flat reflecting plate 28 that has come from the side of the to-be-inspected object 7 and to emit the remaining part thereof toward the back surface of the reference plate 27 while restraining its reflection. The details of the light-quantity ratio adjusting film are described in the specification of Japanese Patent Application No. 2004-276434. A light-quantity ratio adjusting filter to which a light-quantity ratio adjusting film that has the foregoing functions is attached may be removably disposed on the optical path between the reference plate 27 and the to-be-inspected object 7, without attaching the light-quantity ratio adjusting film to the reference surface 27*a* of the reference plate 27 as described in the specification of No. 2004-276434.

In the interference optical system 20, the measuring beam that has passed through the reference surface 27*a* of the reference plate 27 passes through the to-be-inspected object 7 twice during its reciprocation between the reference surface 27*a* and the reflecting surface 28*a* of the flat reflecting plate 28. At this time, the measuring beam causes a disorder in the wave front resulting from, for example, the uneven thickness of the object 7, and returns to the reference surface 27*a* of the reference plate 27 in the form of to-be-inspected transmitted light. This to-be-inspected transmitted light passes through the reference surface 27*a*, and interferes with reference light, thus making it possible to obtain interference light that has phase information such as the thickness non-uniformity of the object 7. The resulting interference light is converged by the collimator lens 26, and enters the beam splitter 25. Apart of the interference light passes through the beam splitter 25, and enters the image pickup section 30.

The image pickup section 30 is made up of an image forming lens 31 and an image pickup camera 32. For example, the image pickup camera 32 has an image pickup surface 33 disposed at an image formation position at which the image forming lens 31 forms an image. The image pickup surface 33 is an image pickup surface of a CCD image sensor including, for example, a photodiode (not shown) that generates an electric charge corresponding to the intensity of light received thereon and a CCD (not shown) that transfers an electric charge stored in the photodiode. Interference-fringe image information that has phase information about the to-be-inspected object 7 during the momentary image pickup period is obtained by interference light received on the image pickup surface 33 during the momentary image pickup period mentioned above. This interference-fringe image information is converted into a video signal according to an interlace scanning method based on, for example, the NTSC (National Television System Committee) standard, and is output.

As shown in FIG. 1, the analyzer 4 includes an image generating portion 41 that generates an interference fringe image based on a video signal output from the image pickup camera 32, a plurality of fringe analyzing portions 42 that analyze fringes of an interference fringe image generated by the image generating portion 41 so as to obtain phase information, such as thickness non-uniformity, about the to-be-inspected object 7 during the momentary image pickup period, and the synchronization signal generating portion 43 that, based on a video signal output from the image pickup camera 32, sets the momentary image pickup period so as to be contained in a light reception acceptable period of the image pickup surface 33, then generates a synchronization signal by which timing at which the AOM13 is driven is controlled, and outputs this synchronization signal to the AOM driver 14.

Based on a synchronization signal output from the synchronization signal generating portion 43, an AOM driving pulse signal is output from the AOM driver 14. This AOM driving pulse signal regulates the momentary image pickup period. The AOM 13 changes the emitted direction of a measuring beam emitted from the collimator lens 12 only during the output of the pulse signal, and allows the measuring beam (more specifically, first-order diffracted light of the measuring beam generated there) to enter the reflecting mirror 15.

Figure 3:
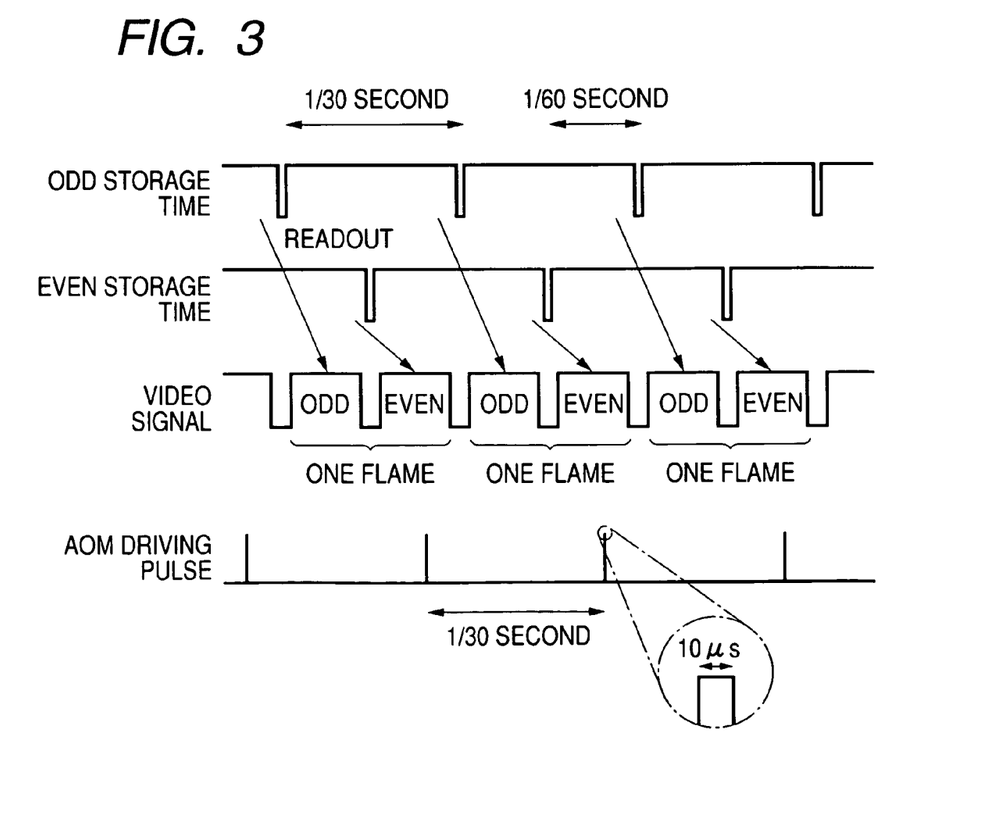
FIG. 3 shows a setting example of a momentary image pickup period.

FIG. 3 shows an example in which the momentary image pickup period is set, i.e., an example of timing at which an AOM driving pulse signal is generated. In FIG. 3, it is assumed that the image pickup surface 33 of the image pickup camera 32 serves as a CCD image sensor and that a signal charge is transferred from this CCD image sensor according to the interline transfer method, and is read by frame readout conforming to the interlace system of the NTSC standard. In more detail, in the example of FIG. 3, the charge storage periods (i.e., light reception acceptable periods) of an odd field and an even field are each 1/30 second, and are overlapped with each other by 1/60 second. The odd field and the even field are alternately read in this order. One frame is constructed of a pair of odd and even fields. An AOM driving pulse signal is generated only once with a width of 10 μs approximately at the center of a period during which the charge storage periods of the odd and even fields both of which form one frame are overlapped with each other.

In more detail, a momentary image pickup period of 10 μs is set once for each frame that is read in a 1/30-second cycle, and an electric charge is simultaneously stored for each couple of odd and even fields forming each frame only during this momentary image pickup period. Therefore, it becomes possible to obtain an interference fringe image having no blur in each frame. The period of 10 μs can be regarded as the movement amount of the object 7 during this period corresponding to, on the image pickup surface 33, less than half the pixel size of the image pickup surface 33.

On the other hand, the image generating portion 41 is made up of a memory in which an image processing program, data about video signals to be processed, etc., are stored, a CPU that makes an image processing calculation, etc. Each of the fringe analyzing portions 42 is made up of a memory in which a fringe analysis program, data about interference fringe images to be processed, etc., are stored, a CPU that makes a fringe analysis calculation, etc. For example, in a case where the momentary image pickup periods are set during a relatively short predetermined time, each of the fringe analyzing portions 42 can perform each fringe analysis based on interference-fringe image information obtained during each momentary image pickup period in a parallel manner. In a case where a plurality of fringe analyses cannot be performed by a single analyzer, an analyzer used for image processing and a plurality of analyzers used for fringe analysis may be provided so that each fringe analysis can be performed by each of the analyzers (computers) individually and in parallel.

Each fringe analyzing portion 42 makes a fringe analysis according to, for example, the Fourier transform analysis method. This Fourier transform analysis method is known as an analysis technique according to which subfringe interferometry can be performed based on a piece of interference-fringe image information. The details of this Fourier transform analysis method are described in, for example, "Foundation of Subfringe Interferometry" of "OPTICS", Vol. 13, No. 1 (February, 1984), pp. 55-65. When the Fourier transform analysis method is employed, high-frequency spatial carrier fringes (spatial carrier frequency) need to be superimposed on interference light. In the apparatus of the present embodiment, the spatial carrier fringes can be introduced by inclining the reflecting surface 28*a* of the flat reflecting plate 28 at a slight angle of $\epsilon$, predetermined angle, with respect to the reference surface 27*a* of the transmission type reference plate 27.

If the to-be-inspected object 7 is a film material such as that mentioned above, fringe-like patterns that extend in substantially parallel with each other will be often formed on the object 7. These fringe-like patterns occur depending on the quality of the film material or the manufacturing method thereof. For example, fringe-like patterns are known which occur in such a manner as to extend in substantially parallel with the longitudinal direction of the film material. These fringe-like patterns appear on an interference fringe image as relatively high-frequency components, and hence there is a possibility that these patterns will approximate the frequency patterns of the spatial carrier fringes mentioned above. Such spatial carrier fringes are removed in an analysis process, however, if an approximation lies between the fringe-like pattern of the film material and the frequency pattern of the spatial carrier fringe, it will become difficult to remove the spatial carrier fringes, and there is a fear that an adverse influence will be exerted on analytical results. Therefore, in the apparatus of the present embodiment, in order to make a clear distinction between the fringe-like pattern of the film material and the frequency-pattern of the spatial carrier fringe, the inclination-direction of the reflecting surface 28a of the flat reflecting plate 28 relative to the reference surface 27a of the reference plate 27 is predetermined so that the spatial carrier fringe becomes substantially perpendicular to the fringe-like pattern of the film material (for example, in a case where fringe-like patterns extending in substantially parallel with the longitudinal direction of the film material occur, the inclination direction of the reflecting surface 28a of the flat reflecting plate 28 is made substantially parallel with the longitudinal direction of the film material).

It is known that some of the film materials mentioned above exhibit a birefringence phenomenon resulting from the optical anisotropy of the molecular structure thereof. There is a fear that the occurrence of birefringence will cause a decrease in the contrast of interference fringes and will exert an adverse influence on measurement. Therefore, in the apparatus of the present embodiment, if the to-be-inspected object 7 has optical anisotropy, a measuring beam is changed into a linearly polarized beam, for example, by disposing a linear polarization filter on the optical path of the measuring beam, and the direction of the transmission axis of the linear polarization filter is adjusted, so that the oscillation direction in the electric field of the linearly polarized light can be adjusted in accordance with the optical axis of the object 7 so as to control the birefringence.

Next, a description will be given of an optical interferometry method for measuring a moving object according to an embodiment of the present invention (hereinafter, also referred to as a "method of the present embodiment"). The method of the present embodiment is carried out according to the following steps using the moving-object measuring interferometric apparatus mentioned above.

(1) The moving-object measuring interferometric apparatus is set as shown in FIG. 1 and FIG. 2.

(2) A laser beam is emitted from the semiconductor laser light source 11. This laser beam is collimated by the collimator lens 12 into a measuring beam, and is allowed to enter the AOM 13 (light beam output step). The AOM 13 is not driven at this stage. Therefore, the measuring beam admitted to the AOM 13 enters neither the interference optical system 20 nor the to-be-inspected object 7.

(3) The image pickup camera 32 is driven to obtain a video signal. At this stage, the to-be-inspected object 7 is not irradiated with the measuring beam, and hence interference-fringe image information cannot be obtained.

(4) Based on a video signal emitted from the image pickup camera 32, a synchronization signal is generated by the synchronization signal generating portion 43, and is output to the AOM driver 14. Accordingly, an AOM driving pulse signal is output from the AOM driver 14 as shown in FIG. 3. Only during a momentary image pickup period during which this AOM driving pulse signal is output, the measuring beam is admitted to the interference optical system 20 via the AOM 13, the slit plate 16, and the reflecting mirror 15 (image pickup timing control step).

(5) The measuring beam admitted to the interference optical system 20 during the momentary image pickup period enters the transmission type reference plate 27 via the divergent lens 21, the collimator lens 22, the convergent lens 23, the pinhole 24a, the beam splitter 25, and the collimator lens 26. At the reference surface 27a of the reference plate 27, the measuring beam is then divided into a light beam acting as a reference light beam while being reflected in the opposite direction by the reference surface 27a and a light beam used to irradiate the object 7 therewith while passing through the reference surface 27a. The light beam with which the object 7 is irradiated passes through the object 7, is then reflected by the reflecting surface 28a of the flat reflecting plate 28, and passes through the object 7 again. Thereafter, this light beam returns to the reference plate 27 as a to-be-inspected transmitted light beam, and passes through the reference surface 27a. The light beam is then combined with a reference light beam, so that interference light can be obtained (interference light generation step).

(6) Interference-fringe image information that has phase information, such as thickness non-uniformity or fringe-like patterns of the object 7 during the momentary image pickup period, is obtained by the interference light received on the image pickup surface 33 during the momentary image pickup period using the image pickup camera 32 (image pickup step) . This image information is converted into a video signal, and is output to the image generating portion 41.

(7) In the image generating portion 41, an interference fringe image corresponding to each momentary image pickup period is generated in sequence based on the video signal input thereto, and is output in sequence to each of the fringe analyzing portions 42.

(8) In each of the fringe analyzing portions 42, each of the interference fringe images input thereto is subjected to a fringe analysis according to the Fourier transform analysis method, so that phase information, such as thickness non-uniformity or fringe-like patterns of the object 7 during each momentary image pickup period, can be obtained.

According to the phase information obtained therein, a determination is made as to whether the object 7 is satisfactory or unsatisfactory as a product. If unsatisfactory, an unsatisfactory part of the object 7 can be discarded later by specifying the unsatisfactory part according to timing at which an interference fringe image is picked up, or manufacturing conditions of the object 7 or the like can be changed by feeding back the measurement result for the control of the manufacturing conditions or the like.

According to the moving-object measuring interferometric apparatus and the optical interferometry method for measuring a moving object as described above, each momentary image pickup period is set to be contained in each light reception acceptable period of the image pickup surface 33, and hence interference-fringe image information, which is identical with that obtained by being picked up in a state in which the to-be-inspected object 7 is stationary, can be reliably obtained at intervals of a predetermined time even when a general-purpose CCD image sensor for dynamic images is used. Therefore, the to-be-inspected object 7 flowing along the production line can undergo in-line measurement.

Additionally, a measuring beam continuously output from the general-purpose semiconductor laser light source 11 can be projected onto the to-be-inspected object 7 only during the momentary image pickup period by using the AOM 13. Therefore, the apparatus can be realized at lower cost than when an expensive pulsed laser is used.

Additionally, the light-quantity ratio adjusting film is attached to the reference surface 27a of the reference plate 27, and the highly reflective film is attached to the reflecting surface 28a of the flat reflecting plate 28. Therefore, the contrast of an interference fringe image to be picked up can be heightened, and measurement can be performed with high accuracy.

Although the embodiment of the present invention has been described as above, the present invention can be modified in various forms without being limited to the above embodiment.

For example, in the above embodiment, the light deflecting section (AOM 13) provided with the AO element that changes the emitted direction of a measuring beam by an acoustooptic effect is used as an image pickup timing control section. Instead, it is possible to use a light deflecting section provided with an EO element that changes the emitted direction of a measuring beam by an electrooptic effect, or use a light deflecting section that changes the emitted direction of a measuring beam by changing the angle of the reflecting mirror 15 with, for example, a piezoelectric element, or use a mechanical chopper or a liquid crystal shutter that opens the optical path of a measuring beam only during a momentary image pickup period and that shuts off the optical path thereof during the other period. It is, as a matter of course, possible to use a pulsed laser, a high-speed image pickup camera, and a driver that drives these elements as the image pickup timing control section.

Additionally, in the above embodiment, a fringe analysis is performed according to the Fourier transform analysis method. Instead, it is possible to employ a fringe analysis technique in which a fringe scan analysis is made from one piece of wave front information by performing a phase shift by use of polarized light, as disclosed in Japanese Patent No. 2821685.

Additionally, in the above embodiment, a CCD image sensor is employed as an example for forming the image pickup surface 33, and a charge transfer method, a readout method, and a scan method are described as above. However, these are merely examples. For example, a frame transfer method or a frame interline transfer method can be employed as the charge transfer method, a field readout method or an all-pixel readout method can be employed as the readout method, and a progressive scan method can be employed as the scan method. The image pickup surface 33 can be formed by using another image pickup element such as a CMOS image sensor.

Additionally, in the above embodiment, the long film material is used as a to-be-inspected object. However, according to the present invention, various moving to-be-inspected objects can be measured. For example, the present invention can be applied to measurement performed when a plurality of to-be-inspected objects separated from each other are moving in sequence. The present invention can also be applied to the measurement of a to-be-inspected object that is opaque with respect to a measuring beam. In this case, there is no need to provide the flat reflecting plate 28. The shape of the to-be-inspected object is not limited to a flat one. For example, the present invention can be applied to the measurement of a to-be-inspected object whose surface is spherical, such as a ball bearing or an optical lens.

Additionally, in the above embodiment, the Fizeau interferometric apparatus is used. Instead, the present invention can be applied to other interferometric apparatuses, such as a Michelson interferometer, a Mach-Zehnder interferometer, or an Abramson grazing-incidence interferometer.

According to the moving-object measuring interferometric apparatus and the moving-object measuring optical interferometry method of the present invention, the structure is formed as described above, and, especially, the momentary image pickup period is set to be contained in the light reception acceptable period of the image pickup surface. Therefore, even when a general-purpose image sensor for dynamic images is used, the same interference-fringe image information as the information about an image taken when a to-be-inspected object is stationary can be reliably obtained. Therefore, a to-be-inspected object whose part to be measured is moved in sequence can undergo in-line measurement.

Additionally, if a light deflecting section for changing the emitted direction of a measuring beam especially by an acoustooptic effect so that the measuring beam can be projected onto the to-be-inspected object only during the momentary image pickup period is used as the image pickup timing control section, the measuring beam can be instantaneously projected by use of, for example, a general-purpose laser beam source without using an expensive pulsed laser. Therefore, the apparatus can be realized at low cost.

Additionally, in the interferometric apparatus including the transmission type reference plate and the reflecting plate, a light-quantity ratio adjusting film is attached to the reference surface of the transmission type reference plate, and a highly reflective film is attached to the reflecting surface of the reflecting plate. Alternatively, a light-quantity ratio adjusting filter to which the light-quantity ratio adjusting film is attached is removably disposed between the reference surface of the transmission type reference plate and the to-be-inspected object, and a highly reflective film having high reflectance with respect to the measuring beam is attached to the reflecting surface of the reflecting plate. Accordingly, the contrast of an interference fringe image to be picked up can be heightened, and hence the interferometric apparatus can perform measurement with high accuracy.

The entire disclosure of each and every foreign patent application from which the benefit of foreign priority has been claimed in the present application is incorporated herein by reference, as if fully set forth.

What is claimed is:

1. A moving-object measuring interferometric apparatus for measuring a moving to-be-inspected object by optical interferometry, the to-be-inspected object moving along a conveyor path, the apparatus comprising:
   a light beam output section that outputs a measuring beam;
   an interference optical system that obtains interference light by projecting the measuring beam onto the to-be-inspected object as the to-be-inspected object is moving along the conveyor path at a predetermined speed, wherein light reflected from the to-be-inspected object or light having passed through the to-be-inspected object interferes with reference light;
   an image pickup section that obtains image information by receiving the interference light on an image pickup surface; and
   an image pickup timing control section that sets a momentary image pickup period during which the to-be-inspected object can be regarded as being substantially stationary with respect to the interferometric apparatus so as to be contained in a light reception acceptable period of the image pickup surface and controls the interference light so that the interference light enters the image pickup surface only during the momentary image pickup period;

wherein the image pickup section obtains interference-fringe image information that has phase information about the to-be-inspected object during the momentary image pickup period from the interference light received on the image pickup surface during the momentary image pickup period.

2. The moving-object measuring interferometric apparatus of claim 1, wherein the image pickup timing control section changes an emitted direction of the measuring beam so that the measuring beam is projected onto the to-be-inspected object only during the momentary image pickup period.

3. The moving-object measuring interferometric apparatus of claim 2, wherein the image pickup timing control section comprises a light deflecting section that changes the emitted direction of the measuring beam by an acoustooptic effect.

4. The moving-object measuring interferometric apparatus of claim 1, wherein, the movement amount of the to-be-inspected object during the momentary image pickup period, is less than half the pixel size of the image pickup surface.

5. The moving-object measuring interferometric apparatus of claim 1, further comprising a transmission type reference plate disposed on an optical path of the measuring beam, the measuring beam admitted to a reference surface of the transmission type reference plate being divided into a light beam that is reflected in an opposite direction by the reference surface so as to serve as the reference light and a light beam that passes through the reference surface so as to irradiate the to-be-inspected object.

6. The moving-object measuring interferometric apparatus of claim 5, further comprising, when the to-be-inspected object is transparent with respect to the measuring beam, a reflecting plate disposed to substantially face the transmission type reference plate in a state of situating the to-be-inspected object between the reflecting plate and the transmission type reference plate, the measuring beam that has passed through the to-be-inspected object and that has entered a reflecting surface of the reflecting plate being reflected toward the transmission type reference plate.

7. The moving-object measuring interferometric apparatus of claim 6, wherein: a light-quantity ratio adjusting film is attached to the reference surface of the transmission type reference plate, the light-quantity ratio adjusting film comprising at least one light reflection absorbing layer and at least one dielectric reflection preventing layer stacked on the reference surface of the transmission type reference plate in this order when viewed from the reference plate, the light-quantity ratio adjusting film reflecting a part of the measuring beam that enters from a side of the reference surface and absorbing a remaining part of the measuring beam and emitting a still remaining part of the measuring beam toward the to-be-inspected object, the light-quantity ratio adjusting film further absorbing a part of return light from the reflecting plate that enters from a side of the to-be-inspected object and emitting a remaining part of the return light toward the reference surface so as to serve as the to-be-inspected transmitted light while being controlled not to be reflected; and a highly reflective film that reflects the measuring beam with high reflectance is attached to the reflecting surface of the reflecting plate.

8. The moving-object measuring interferometric apparatus of claim 6, wherein a light-quantity ratio adjusting filter is removably disposed between the reference surface of the transmission type reference plate and the to-be-inspected object; and a highly reflective film that reflects the measuring beam with high reflectance is attached to the reflecting surface of the reflecting plate;

the light-quantity ratio adjusting filter comprising a light-quantity ratio adjusting film having a multi-layer film structure, the light-quantity ratio adjusting film including at least one light reflection absorbing layer and at least one dielectric reflection preventing layer stacked at least one of on a surface of a transparent substrate facing the to-be-inspected object and on a surface of the transparent substrate facing the reference surface in this order when viewed from the reference surface;

the light-quantity ratio adjusting film reflecting a part of incident light coming from a side of the surface of the transparent substrate facing the reference surface and absorbing a remaining part of the incident light and emitting a still remaining part of the incident light toward the to-be-inspected object;

the light-quantity ratio adjusting film further absorbing a part of return light from the to-be-inspected object coming from a side of the surface of the transparent substrate facing the to-be-inspected object and emitting a remaining part of the return light toward the reference surface so as to serve as the to-be-inspected light while being controlled not to be reflected.

9. The moving-object measuring interferometric apparatus of claim 1, further comprising an analysis section that makes a fringe analysis based on the interference-fringe image information so as to obtain the phase information.

10. The moving-object measuring interferometric apparatus of claim 9, wherein a plurality of the momentary image pickup periods are set during a predetermined time, and each fringe analysis based on the interference-fringe image information obtained during each momentary image pickup period is performed in a parallel manner.

11. The moving-object measuring interferometric apparatus of claim 9, wherein the analysis section makes the fringe analysis according to a Fourier transform analysis method, and the interference optical system is disposed so that spatial carrier fringes required for the Fourier transform analysis method are superimposed on the interference light.

12. The moving-object measuring interferometric apparatus of claim 11, wherein, when the to-be-inspected object has fringe-like patterns that extend in substantially parallel with each other, the interference optical system is disposed so that the spatial carrier fringe becomes substantially perpendicular to the fringe-like pattern.

13. The moving-object measuring interferometric apparatus of claim 6, wherein, when the to-be-inspected object has optical anisotropy, the measuring beam is formed to be linearly-polarized light, and an oscillation direction in an electric field of the linearly polarized light is adjusted in accordance with a direction of an optical axis of the to-be-inspected object so as to restrain birefringence.

14. An optical interferometry method for measuring a moving to-be-inspected object while using an interferometric apparatus, the method comprising:

outputting a measuring beam;

obtaining interference light by projecting the measuring beam onto the to-be-inspected object as the to-be-inspected object is moving along the conveyor path at a predetermined speed and by allowing light reflected from the to-be-inspected object or light that has passed through the to-be-inspected object to interfere with reference light;

receiving the interference light by an image pickup surface so as to obtain image information; and setting a momentary image pickup period during which the to-be-inspected object can be regarded as being substantially stationary with respect to the interferometric apparatus so as to be contained in a light reception acceptable period of the image pickup surface and controlling the interference light so that the interference light enters the image pickup surface only during the momentary image pickup period; and obtaining interference-fringe image information that has phase information about the to-be-inspected object during the momentary image pickup period by the interference light received at the image pickup surface during the momentary image pickup period, and obtaining the phase information by making a fringe analysis based on the interference-fringe image information.

* * * * *